(12) United States Patent
Angelsen et al.

(10) Patent No.: US 7,300,403 B2
(45) Date of Patent: Nov. 27, 2007

(54) WIDE APERTURE ARRAY DESIGN WITH CONSTRAINED OUTER PROBE DIMENSION

(76) Inventors: Bjørn A. J. Angelsen, Bugges veg 4B, Trondheim (NO) N7051; Tonni F. Johansen, Osloveien 6, Trondheim (NO) N7018; Rune Hansen, Kaarli, Stadsbygd (NO) 7105; Peter Naesholm, Brøset veien 145d, Trondheim (NO) N7048

( * ) Notice: Subject to any disclaimer, the term of this patent is extended or adjusted under 35 U.S.C. 154(b) by 303 days.

(21) Appl. No.: 10/894,954

(22) Filed: Jul. 20, 2004

(65) Prior Publication Data

US 2006/0036176 A1    Feb. 16, 2006

(51) Int. Cl.
*A61B 8/00* (2006.01)
(52) U.S. Cl. ...................................... 600/447
(58) Field of Classification Search ........ 600/443–448, 600/454–456, 472; 128/916; 73/625–626, 73/644
See application file for complete search history.

(56) References Cited

U.S. PATENT DOCUMENTS

| | | | | |
|---|---|---|---|---|
| 4,459,853 A | * | 7/1984 | Miwa et al. | 73/626 |
| 4,567,895 A | * | 2/1986 | Putzke | 600/445 |
| 4,569,231 A | * | 2/1986 | Carnes et al. | 73/626 |
| 4,641,660 A | * | 2/1987 | Bele | 600/459 |
| 4,991,151 A | * | 2/1991 | Dory | 367/150 |
| 5,027,659 A | * | 7/1991 | Bele et al. | 73/626 |
| 6,605,043 B1 | * | 8/2003 | Dreschel et al. | 600/459 |
| 6,865,140 B2 | * | 3/2005 | Thomenius et al. | 367/155 |
| 2004/0158154 A1 | * | 8/2004 | Hanafy et al. | 600/446 |

* cited by examiner

*Primary Examiner*—Francis J. Jaworski
(74) *Attorney, Agent, or Firm*—Cohen Pontani Lieberman & Pavane LLP

(57) ABSTRACT

The invention presents solutions for large apertures of an ultrasound array under given dimension constraints given by the application for the ultrasound probe, for example by an endoluminal application. The invention has applications to annular arrays for 2D and 3D imaging, and also to linear or curvilinear arrays for 2D and 3D imaging. The invention further provides large aperture of arrays for dual frequency band operation with large difference between the dual bands.

17 Claims, 5 Drawing Sheets

WIDE APERTURE ARRAY DESIGN WITH CONSTRAINED OUTER PROBE DIMENSION

BACKGROUND OF THE INVENTION

1. Field of the Invention

The present invention is directed to technology and designs of ultrasound transducer arrays for widest possible apertures with dimension constraints on the total probe. The invention also has application for ultrasound arrays with simultaneous operation in at least two frequency bands for imaging of ultrasound contrast agents and elastography imaging of tissue.

2. Description of the Related Art

The focal diameter of the beam from an ultrasound array is inversely proportional to the diameter of the array aperture. In many situations, the outer dimensions of the probe are limited by constraints from the clinical application, such as imaging from the vagina, the rectum, or other endoluminal and surgical imaging. These constraints put a limit on the aperture diameter of the ultrasound array, hence putting a lower limit on the beam focal diameter and hence the spatial resolution for an ultrasound imaging system.

The invention presents solutions of array designs that maximize the array aperture in relation to constraints on the outer dimension of the probe.

There is also a need to transmit ultrasound pulses with frequency components in so widely separate frequency bands, that it is difficult with current technology to transmit the different frequency bands from the same part of the array surface. The invention provides a solution to this problem.

SUMMARY OF THE INVENTION

The invention presents array designs that provide large array radiating apertures for minimal focal width of the beam, in situations where the outer diameter of the probe is limited by the application. The array radiating surface is divided into several regions of array elements that is arranged spatially in relation to the center of the array surface, where the radiating surface of each region is physically retracted from the radiating surface of regions that are located more central on the array. With this solution, one can use radiating surfaces close to normal to the beam direction, allowing for wider apertures with the given constraints of the total dimension.

The invention is particularly applicable to annular arrays with mechanical scanning of the beam direction in one dimension (for two-dimensional (2D) imaging) or two dimensions (for three-dimensional (3D) imaging). The invention is further applicable to the aperture in the elevation direction of phased and switched linear or curvilinear arrays. The beam can then optionally be direction scanned in the elevation direction (for 3D imaging) by mechanically moving the array in the elevation direction.

The invention further has applications for arrays with operation of ultrasound pulses in two separate frequency bands, using largest possible apertures with the given dimension constraints on the ultrasound probe.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1:
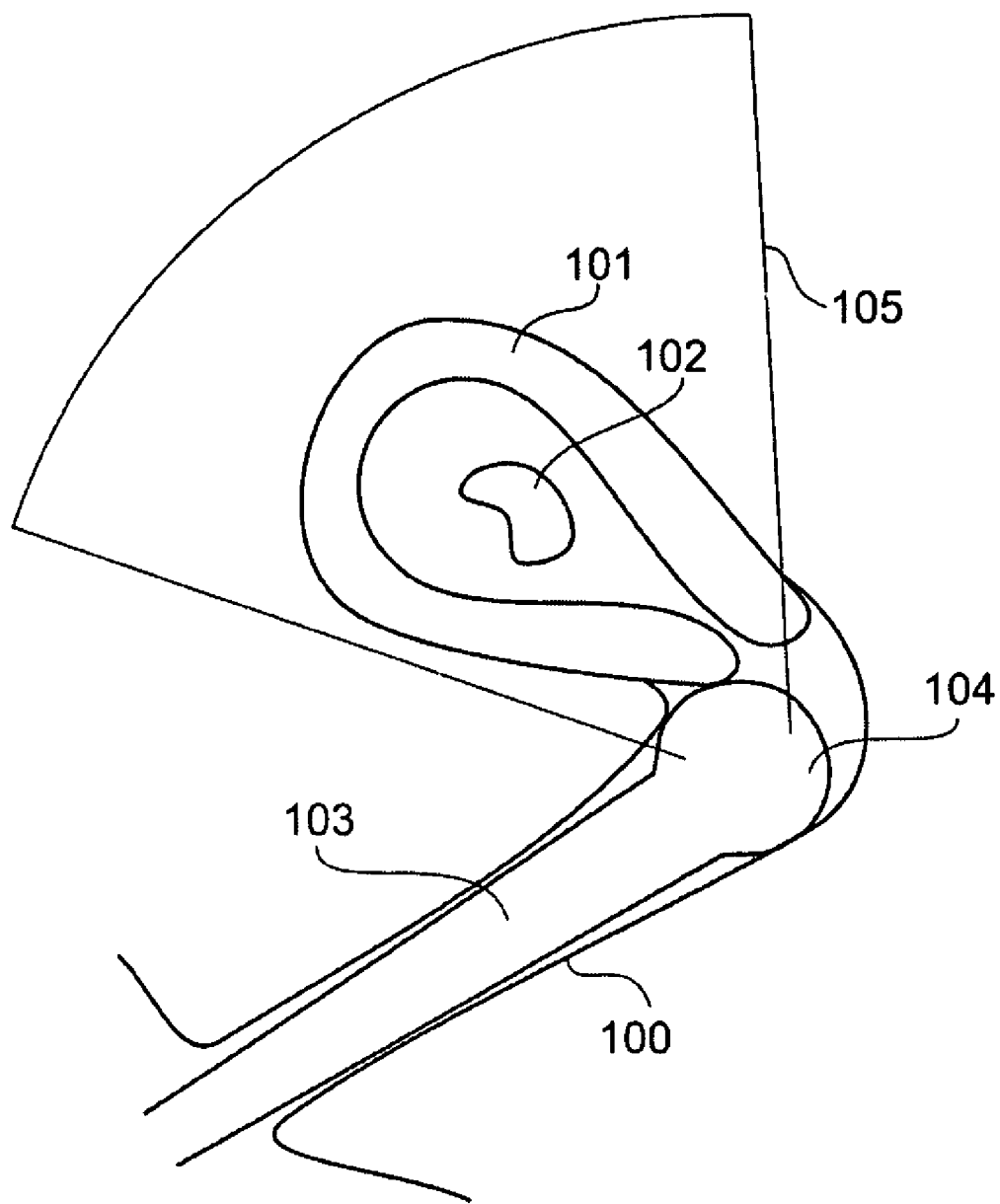
FIG. 1 illustrates transvaginal imaging of a fetus as a typical application with dimension constraints on the ultrasound probe.

FIG. 1 illustrates a typical problem of constraints to the ultrasound array aperture given by a clinical application. Transvaginal imaging of a small fetus is chosen as an example that serves as an illustration for many other imaging situations, particularly endoluminal imaging from the rectum, colon, surgical imaging, etc. 100 illustrates the vaginal channel (endoluminal channel), with the uterus 101 and a fetal object 102 to be imaged.

The vaginal probe is illustrated as 103 with an expanded spherical or cylindrical tip 104 which marks the outer dimensions of the probe tip that is allowed by the endoluminal channel. The ultrasound beam direction is then typically scanned within a sector 105 from an ultrasound array at the probe tip, to image the object within the sector. The beam direction can additionally also be scanned normal to the drawing to provide scanning within a 3D volume for 3D imaging of the object within the scanned region.

Figure 2:
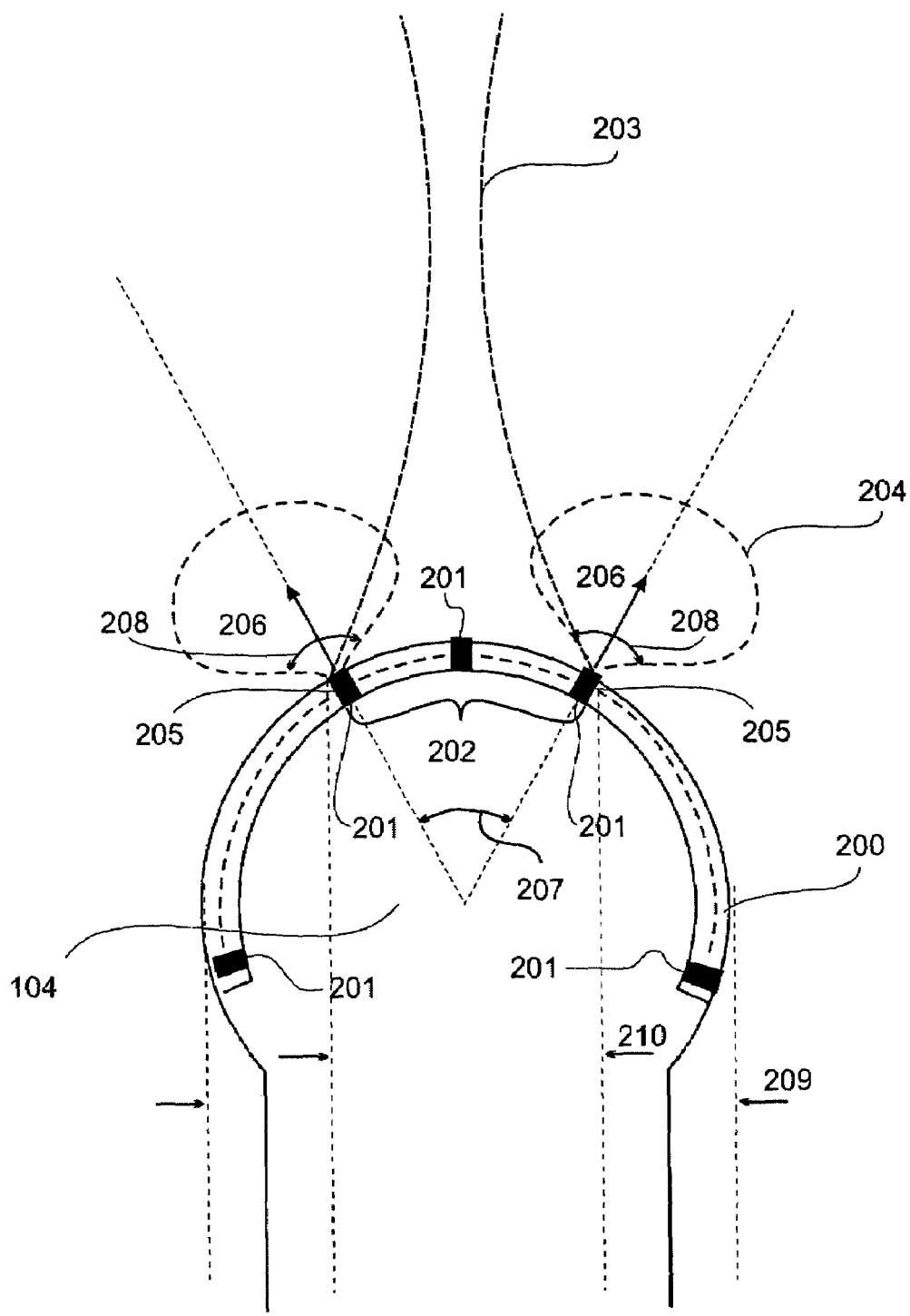
FIG. 2 illustrates a prior art ultrasound probe for endoluminal ultrasound imaging.

FIG. 2 shows an example of a prior art curvilinear switched array that is used for such imaging. The figure shows a cross section through the middle of the array in the azimuth direction, which is the direction for 2D scanning of the beam. The array is close to cylindrical in the direction normal to the paper, which is termed the elevation direction of the array. 200 shows the array that is curved around the probe tip 104 in a cylindrical manner, with example array elements illustrated as 201. The active array aperture for a selected beam 203 is composed of a sub-group 202 of array elements that is selectively from the total group 200 of array elements connected to the instrument to generate the imaging beam 203. A requirement for the sub-group 202 to efficiently form an ultrasound beam with limited side-lobe level, is that the element beam profiles 204 from the outer elements 205 of the selected sub-group aperture sufficiently overlaps.

This can be reformulated that the divergence angle 207 of the element normals 206 from the outer elements 205 must be less than the opening angle 208 of the element beam profiles 204. In practice this gives an opening angle 207 of the aperture of 45 deg, which for a total diameter 209 of the probe tip of 30 mm gives a practical aperture 210 of 11 mm.

Figure 3:
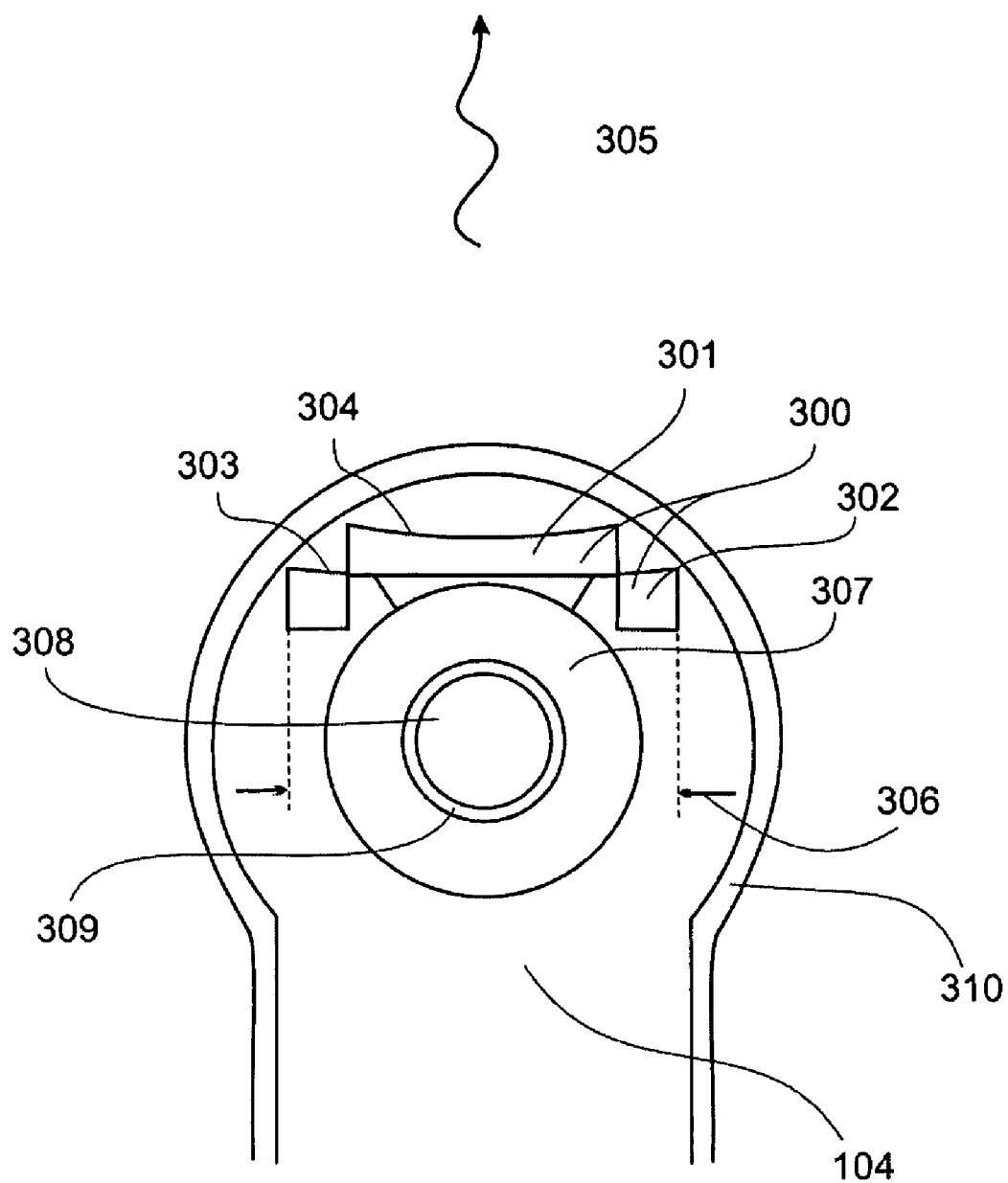
FIG. 3 illustrates an embodiment of an annular array for 2D and 3D imaging according to the invention, where the array aperture is extended through retracting an outer group of elements from the central elements.

An example embodiment according to the invention using an annular array which provides a much larger aperture than that obtained with the array in FIG. 2 with the same given constraints on the total probe diameter, is shown in FIG. 3. The probe tip 104 is covered with a spherical dome 310 of acoustically transparent material. The dome encloses in this example an annular array 300 of concentric elements, composed of a central group 301 of elements surrounded by a second group 302 of elements whose front surface 303 is retracted from the front surface 304 of the central group. The dome is filled with an acoustically transparent fluid so that the array radiates from the front surfaces 303 and 304 in the direction 305. The array is mounted on a structure 307 that is connected to a rotating shaft 308 that rotates in bearings 309.

It is often necessary from constraints of the rotating mechanism 307, that the central group 301 of concentric array elements must be positioned as close to the dome 310 as possible, hence limiting the possible diameter of the central group. It is also an advantage for acoustical reasons that the radiating surfaces of the array (303, 304) are as close to the dome 310 as possible. An array structure divided into sub-groups, where the radiating front surfaces of each group is retracted from the radiating surfaces of the inner groups as exemplified by the two groups 301 and 302 in FIG. 3, hence allows the maximal total radiating aperture of the array under the given constraints. A typical aperture of ~20 mm diameter within a probe tip of 30 mm outer diameter can be achieved.

The direction of the beam is then scanned by rotating the array structure in the bearings 309, which for example can be mounted in a fork which can be rotated around a $2^{nd}$ axis, like in U.S. Pat. No. 6,780,153, issued Aug. 24, 2004. This allows 3D scanning of the ultrasound beam from the annular array structure in two angular directions.

To form a combined beam of the apertures of the central group and retracted groups of elements, the signals from each group are delayed relative to signals from outer retracted groups an amount defined by the length of the relative retraction, according to well known beam-forming requirements.

In some situations, for example ultrasound contrast agent imaging or tissue characterization, it is desirable to transmit ultrasound pulses in collimated beams with frequency components in widely separated frequency bands, for example with frequency components in limited bands around 500 kHz and 5 MHz. It is then difficult with current technology to make array structures which can radiate such pulses from the same region of the array surface.

An array design as the one in FIG. 3 provides a solution to this problem, where the outer group of elements 302 for example is designed with a low transmission band (e.g. centered around 500 kHz) and the central group of elements are designed with the high transmission band (e.g. centered around 5 MHz). The high frequency pulse is in such situations used for the imaging, and the design of FIG. 3 then allows a maximal aperture of the imaging group 301 under the given constraints, for narrowest main lobe and lowest side lobes of the beam. This gives best possible spatial and contrast resolution in the image.

The design also provides the widest aperture under the constraints for the low frequency part of the array, to provide a maximally collimated low frequency component of the beam. It is also possible for some applications to remove parts of radiating surface of the low frequency outer annular group of elements and still maintaining a collimated low frequency beam with tolerable increase in side lobe level.

Figure 5:
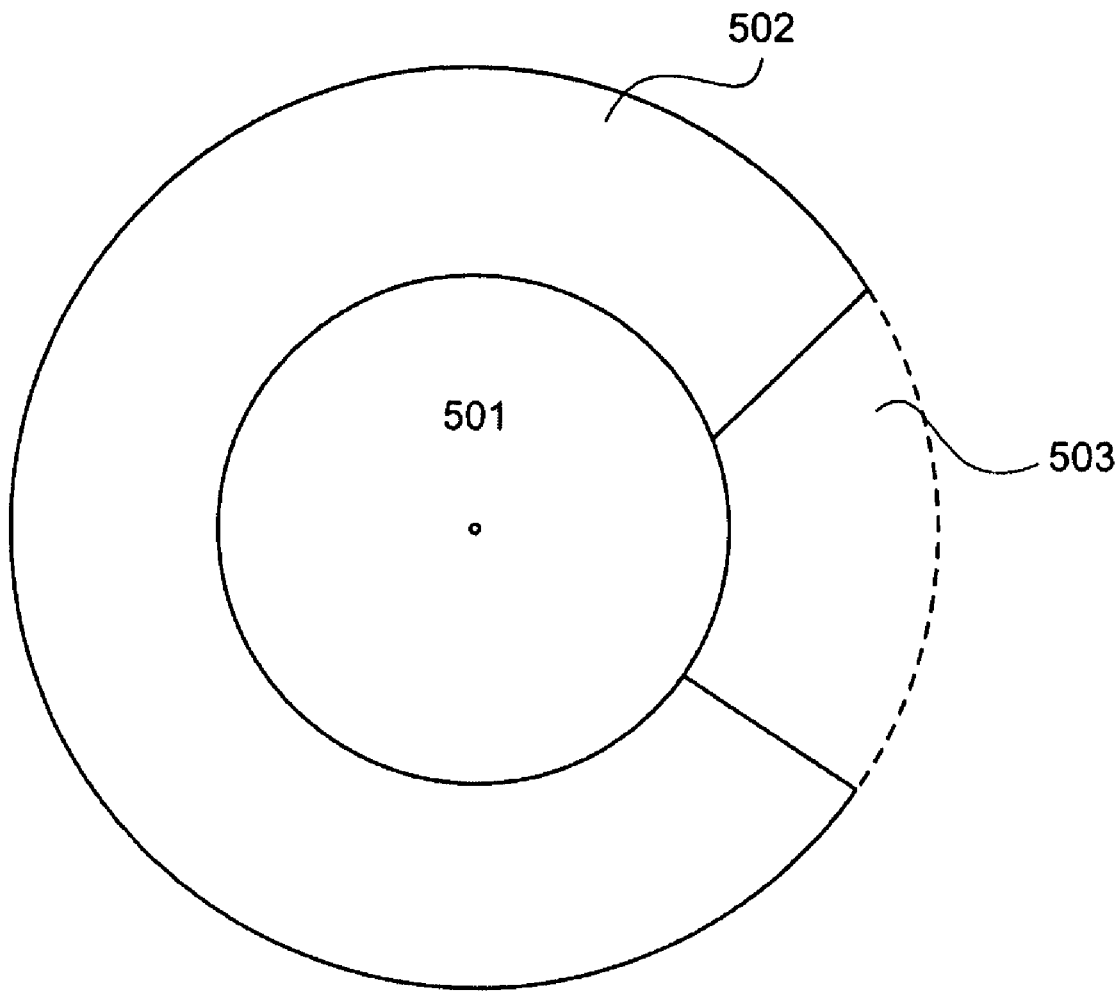
FIG. 5 shows yet another embodiment according to the invention of an annular array where part of an outer annular radiating surface of said array is removed.

Such a situation is illustrated in FIG. 5, where 501 shows the central, high frequency part of the array, and 502 shows the retracted, low frequency part of the array with a portion 503 of the annular elements and their radiating surface removed. Such removal of parts of the elements can allow wider total aperture diameter of the array with given mechanical constraints and with tolerable influence on the beam from the outer part.

For lower separation between the two frequency bands, one can make ultrasound transducer arrays with wide bandwidth or multi band operation with band separation up to the $5^{th}$ harmonic variation of the center frequencies of the bands, for example as described in U.S. Pat. No. 6,645,150 issued Nov. 11, 2003. One would in such situations use the whole aperture of all retracted surfaces at least for the frequency band used for imaging, to provide the widest aperture for the imaging band and hence best resolution in the image. For the lower frequency bands, it is important to use the outer groups of elements for the beam forming, as the collimation of the main lobe of the low frequency beam is then determined by the outer dimension of the aperture.

Capacitive micromachined ultrasound transducers on silicon, so-called cmuts, are under development, where acousto-electric capacitors with a vibrating front membrane are used to radiate and receive ultrasound waves. The cmut vibration membranes can be designed to cover frequency ranges up to ~$10^{th}$ harmonic, hence allowing 500 kHz and 5 MHz to be transmitted from the same radiated surface. More efficient transmit function can be obtained by placing cmut acousto-electric membrane capacitors of different frequencies interleaved on the radiating surface.

These acousto-electric capacitors have an elastic front membrane, so-called drumhead, that is used as the front electrode in a capacitor. Variable voltage over the capacitor will cause the drumhead to vibrate, coupling electric to acoustic energy in the contacting material, and vice versa. The drumheads are much smaller than the ultrasound wave length in the tissue, so that with sufficient density of the drumheads for each frequency, they will for the beam forming create a continuous radiating surface for each frequency. For multi-band operation of an array element, two groups of drumheads interleaved on the elements surface, where one group is composed of wider drumheads for low frequency operation, and the other group is composed of smaller drum-heads for higher frequency operation.

In this case one could use the surface of all retracted groups for both frequency bands, particularly for the frequency band used for imaging, whereas for the low frequency components it still can make sense as above to use only the outer groups of elements to provide the best possible collimated low frequency beam.

Figure 4:
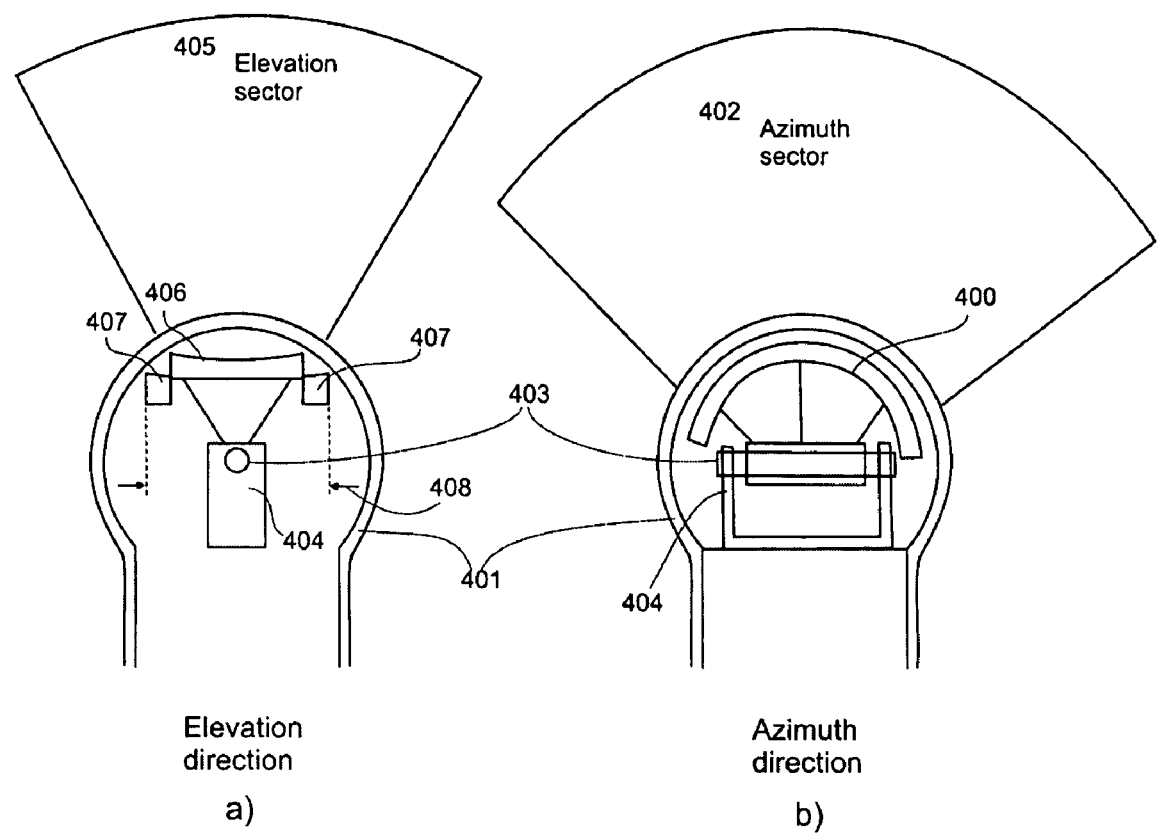
FIG. 4 shows an embodiment according to the invention of a switched curvilinear array with mechanical movement in the elevation direction for 3D imaging.

A design similar to that in FIG. 3 is also useful for the aperture in the elevation direction with linear and curvilinear arrays with electronic scanning of the beam in the azimuth direction, as illustrated in FIG. 4 (the elevation direction is normal to the azimuth direction). Directional beam scanning in the elevation direction can then be done by mechanical rotation as in FIG. 4. In this example embodiment, a curved array 400 is mounted in a fluid-filled dome 401 and is able to radiate beams normal to the array surface from selected groups of elements within a 2D sector 402 in the azimuth direction as shown in FIG. 4b, according to standard methods of beam scanning with switched linear or curvilinear arrays.

In the elevation direction as shown in FIG. 4a, the array is in this example embodiment composed of two groups 406 and 407 of elements, where the radiating front face of outer group 407 is retracted from the radiating front face of the central group 406 of elements. As the radiating front faces of the elements all are close to normal to the beam direction, there will not be the same problem of overlap between the beams from the outer elements as for the curved, state of the art structure described in FIG. 2. Hence, the elevation aperture 408 is increased under the given dimension constraints of the probe, compared to without retraction of the outer group of elements.

For 3D imaging, the array is mounted on a shaft 403 that is mounted in bearings 404 allowing the array to rotate in the elevation direction, normal to the azimuth direction, to emit beams within a sector 405 in the elevation direction. Such elevation scanning is remedied by an actuator and position sensor according to methods known to any-one skilled in the art.

With no elevation scanning of the beam direction, the array 400 does not have to be placed in a fluid filled dome, where the radiating surfaces of the element groups could be smoothened with acoustically transparent material, where the refraction indexes of the material in relation to the tissue is included with the elevation inclination angle of the elements to provide an adequate fixed focus of the elements in front of the array, according to known methods.

One should note that as one in FIGS. 3 and 4 have shown one central group of elements with only one outer group of elements with front surface retracted from the central group of elements, there are situations where one would like to use several groups of elements, where the surface of each group is retracted from the nearest more central group, so that the total of the aperture can be large, while the surface of all element groups are close to the dome.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. An ultrasound probe for radiating an ultrasound beam, and with constraints on an outer ultrasound probe dimension given by application of the probe, wherein:

the probe includes an ultrasound array of elements with radiating front faces arranged at least in one direction close to normal to the ultrasound beam direction, and the radiating front faces define an array radiating surface, the array radiating surface has a defined center or central region and said array elements are divided into at least two groups of array elements with a central group of elements in the central region of said array radiating surface, the radiating surface of each said group of elements is mechanically retracted from the radiating surfaces of groups of elements closer to said center or center region, and wherein the radiating front face of each element in each group is directed, or shaped, or adapted to a lens so that the axes of the beams from said individual elements in the different groups are parallel to or cross one of a plane and an axis common to all groups of elements, so that the total aperture for beam forming with said array can be large within the outer dimension constraint of the probe.

2. The ultrasound probe according to claim 1, wherein said array of elements is an annular array with a center, and said array elements are divided into groups of annular elements, the radiating surface of each of said groups of elements are close to normal to the beam direction and is retracted from said radiating surface of groups of elements closer to said center.

3. The ultrasound probe according to claim 2 wherein said annular array is mounted in a mechanism that allows direction scanning of the ultrasound beam in at least two directions, for three-dimensional ultrasound imaging with said probe.

4. The ultrasound probe according to claim 2, wherein said annular array is mounted in a mechanism that allows direction scanning of the ultrasound beam in at least one direction, for two-dimensional ultrasound imaging with said probe.

5. The ultrasound probe according to claim 1, wherein said array of elements is a linear or curvilinear array with a central axis in the azimuth direction along said array surface, and said array elements are divided in the elevation direction into groups of elements, where the radiating surface of each group of elements is in the elevation direction close to normal to the beam direction and is retracted from the radiating surface of groups of elements closer to said center axis.

6. The ultrasound probe according to claim 5, wherein said linear or curvilinear array can be moved mechanically in said elevation direction whereas the ultrasound beam is electronically direction scanned in said azimuth direction, for direction scanning of the ultrasound beam in at least two directions, for three-dimensional ultrasound imaging with said probe.

7. The ultrasound probe according to claim 6, wherein the ultrasound array is mounted in a fluid filled dome, where both said dome and said fluid are acoustically transparent.

8. The ultrasound probe according to claim 1, wherein for including several of said groups of elements to form a beam, the element signals from each group are given an additive delay in the beam forming in the ultrasound instrument, said delay being determined by the retraction of each group relative to the retraction of the out-most group that participates in the beam forming.

9. The ultrasound probe according to claim 1, wherein said array elements are made as cmut transducers on silicon.

10. The ultrasound probe according to claim 9, wherein different dimension drumheads that operate in different frequency bands are placed interleaved on the radiating surface of said array elements.

11. The ultrasound probe according to claim 1, wherein the radiating surface of at least some of said groups of array elements are made to radiate ultrasound pulses in widely separate frequency bands.

12. The ultrasound probe according to claim 11, wherein all of said groups of array elements are able to operate in a high frequency band, and at least the outer of said groups of elements are able to operate in a low frequency band.

13. The ultrasound probe according to claim 11, wherein the outer groups of said groups of elements are made to operate in a low frequency band, and the remaining, central groups of said groups of elements are made to operate in a high frequency band.

14. The ultrasound probe according to claim 13, wherein said array is an annular array, and where parts of the annular array elements that operate in the low frequency band are removed.

15. The ultrasound probe according to claim 11, wherein said array elements are made as cmut transducers on silicon, with different size drumheads for the different frequency band operation of the elements.

16. An ultrasound probe for radiating an ultrasound beam, and with constraints on an outer ultrasound probe dimension given by application of the probe, wherein:

the probe includes an ultrasound array of elements with radiating front faces arranged at least in one direction close to normal to the ultrasound beam direction, and the radiating front faces define an array radiating surface, wherein said array elements are made as cmut transducers on silicon, and different dimension drumheads that operate in different frequency bands are placed interleaved on the radiating surface of said array elements, the array radiating surface has a defined center or central region and said array elements are divided into at least two groups of array elements with a central group of elements in the central region of said array radiating surface, and wherein the radiating surface of each said group of elements is mechanically retracted from the radiating surfaces of groups of elements closer to said center or center region, so that the total aperture of said array can be large within the outer dimension constraint of the probe.

17. An ultrasound probe for radiating an ultrasound beam, and with constraints on an outer ultrasound probe dimension given by application of the probe, wherein:

the probe includes an ultrasound array of elements with radiating front faces arranged at least in one direction close to normal to the ultrasound beam direction, and the radiating front faces define an array radiating surface, the array elements are made as cmut transducers on silicon, with different size drumheads for different frequency operation of the elements, the array radiating surface has a defined center or central region and said array elements are divided into at least two groups of array elements with a central group of elements in the central region of said array radiating surface, the radiating surface of at least some of said groups of array elements are made to radiate ultrasound pulses in widely separate frequency bands, and wherein the radiating surface of each said group of elements is mechanically retracted from the radiating surfaces of groups of elements closer to said center or center region, so that the total aperture of said array can be large within the outer dimension constraint of the probe.

* * * * *